US012077383B2

(12) United States Patent
Hawkes et al.

(10) Patent No.: US 12,077,383 B2
(45) Date of Patent: Sep. 3, 2024

(54) SYSTEM AND METHODOLOGY FOR FILLING PRESCRIPTIONS

(71) Applicant: REMEDI TECHNOLOGY HOLDINGS, LLC, Towson, MD (US)

(72) Inventors: Kimberly Hawkes, Powell, OH (US); Steven E. Schneider, Lewis Center, OH (US); Mark Stielau, Fennville, MI (US); Richard W Snodgrass, Columbus, OH (US); Thomas P. Hayes, Cambridge (CA)

(73) Assignee: REMEDI TECHNOLOGY HOLDINGS, LLC, Towson, MD (US)

( * ) Notice: Subject to any disclaimer, the term of this patent is extended or adjusted under 35 U.S.C. 154(b) by 794 days.

(21) Appl. No.: 17/025,101

(22) Filed: Sep. 18, 2020

(65) Prior Publication Data

US 2021/0070548 A1 Mar. 11, 2021

Related U.S. Application Data

(63) Continuation of application No. 12/617,075, filed on Nov. 12, 2009, now Pat. No. 10,916,340, which is a
(Continued)

(51) Int. Cl.
*G16H 40/20* (2018.01)
*B65G 1/137* (2006.01)
(Continued)

(52) U.S. Cl.
CPC ............ *B65G 1/1376* (2013.01); *G07F 11/44* (2013.01); *G16H 20/13* (2018.01); *G16H 20/17* (2018.01); *G16H 40/20* (2018.01)

(58) Field of Classification Search
CPC ..... B65G 1/1376; B65G 59/067; G07F 11/44; G07F 17/0092; G16H 20/13; G16H 20/17; G16H 40/20
See application file for complete search history.

(56) References Cited

U.S. PATENT DOCUMENTS 3,013,693 A 12/1961 Griner
3,998,356 A 12/1976 Christensen
(Continued)

OTHER PUBLICATIONS

Combined Chinese Office Action and Search Report dated Nov. 5, 2012 in Chinese Patent Application No. 200980155637 .5 (with English Translation of Categories of Cited Documents).
(Continued)

*Primary Examiner* — Chad A Newton
(74) *Attorney, Agent, or Firm* — Oblon, McClelland, Maier & Neustadt, L.L.P.

(57) ABSTRACT

A pharmacy system and methodology for individually packaged medications and/or supplements assembled into an order for each patient which can be delivered to a long-term care facility or other institution for patient consumption. The process may include receiving a patient's prescription order, automatically dispensing packaged unit doses, and assembling into individually packaged bags for each patient. Various safeguards and measures built into this system and method increase patient safety, eliminate waste, and increase labor efficiency by reducing and/or minimizing the disposal of unused medications and supplements.

10 Claims, 5 Drawing Sheets

Related U.S. Application Data continuation-in-part of application No. 12/559,630, filed on Sep. 15, 2009, now Pat. No. 9,938,082, which is a continuation-in-part of application No. 12/559,601, filed on Sep. 15, 2009, now Pat. No. 9,745,131.

(60) Provisional application No. 61/120,209, filed on Dec. 5, 2008.

(51) Int. Cl.
*G07F 11/44* (2006.01)
*G16H 20/13* (2018.01)
*G16H 20/17* (2018.01)

(56) References Cited

U.S. PATENT DOCUMENTS

| | | |
|---|---|---|
| 4,655,026 A | 4/1987 | Wigoda |
| 4,870,799 A | 10/1989 | Bergerioux et al. |
| 4,880,102 A | 11/1989 | Indreba |
| 4,901,843 A | 2/1990 | Lashyro |
| 4,971,513 A | 11/1990 | Bergerioux et al. |
| 5,054,761 A | 10/1991 | Dietrich et al. |
| 5,061,231 A | 10/1991 | Dietrich et al. |
| 5,104,369 A | 4/1992 | Calvert |
| 5,161,791 A | 11/1992 | Akiyama et al. |
| 5,211,523 A | 5/1993 | Andrada Galan et al. |
| 5,271,703 A | 12/1993 | Lindqvist et al. |
| 5,288,201 A | 2/1994 | Pippin |
| 5,299,907 A | 4/1994 | Dal Pozzo |
| 5,322,406 A | 6/1994 | Pippin et al. |
| 5,392,927 A | 2/1995 | Haverkamp Begemann et al. |
| 5,431,298 A | 7/1995 | Brewer et al. |
| 5,454,688 A | 10/1995 | Pippin |
| 5,468,110 A | 11/1995 | McDonald et al. |
| 5,511,772 A | 4/1996 | Ganz et al. |
| 5,533,606 A | 7/1996 | Yuyama |
| 5,551,822 A | 9/1996 | Pippin et al. |
| 5,564,893 A | 10/1996 | Tacchi et al. |
| 5,582,324 A | 12/1996 | Pippin et al. |
| 5,593,267 A * | 1/1997 | McDonald .......... G07F 17/0092 414/280 |
| 5,597,995 A | 1/1997 | Williams et al. |
| 5,604,692 A | 2/1997 | Yuyama |
| 5,666,492 A | 9/1997 | Rhodes et al. |
| 5,713,718 A | 2/1998 | Okura et al. |
| 5,720,157 A | 2/1998 | Ross |
| 5,755,551 A | 5/1998 | Saeki et al. |
| 5,755,552 A | 5/1998 | Iwasaka et al. |
| 5,768,095 A | 5/1998 | Albaum et al. |
| 5,768,139 A | 6/1998 | Pippin et al. |
| 5,771,657 A | 6/1998 | Lasher et al. |
| 5,772,392 A | 6/1998 | Okura et al. |
| 5,797,515 A | 8/1998 | Liff et al. |
| 5,832,693 A | 11/1998 | Yuyama et al. |
| 5,833,599 A | 11/1998 | Schrier et al. |
| 5,912,818 A | 6/1999 | McGrady et al. |
| 5,930,145 A | 7/1999 | Yuyama et al. |
| 5,934,864 A | 8/1999 | Lyon et al. |
| 5,945,651 A | 8/1999 | Chorosinski et al. |
| RE36,329 E | 10/1999 | Laroche |
| 5,963,453 A | 10/1999 | East |
| 5,970,462 A | 10/1999 | Reichert |
| 5,971,594 A | 10/1999 | Sahai |
| 5,988,858 A | 11/1999 | Yuyama et al. |
| 5,992,742 A | 11/1999 | Sullivan et al. |
| 6,061,607 A | 5/2000 | Bradley et al. |
| 6,064,921 A | 5/2000 | Pippin et al. |
| 6,068,156 A | 5/2000 | Liff et al. |
| 6,101,787 A | 8/2000 | Brintazzoli et al. |
| 6,152,364 A | 11/2000 | Schoonen et al. |
| 6,170,230 B1 | 1/2001 | Chudy et al. |
| 6,170,634 B1 | 1/2001 | Jaquet |
| 6,202,923 B1 | 3/2001 | Boyer et al. |
| 6,206,590 B1 | 3/2001 | Thomas et al. |
| 6,247,890 B1 | 6/2001 | Chang et al. |
| 6,256,967 B1 | 7/2001 | Hebron et al. |
| 6,260,761 B1 | 7/2001 | Peoples, Jr. |
| 6,289,260 B1 | 9/2001 | Bradley et al. |
| 6,308,109 B1 | 10/2001 | Yuyama et al. |
| 6,317,648 B1 | 11/2001 | Sleep et al. |
| 6,347,709 B1 | 2/2002 | Biehl et al. |
| 6,367,232 B2 | 4/2002 | Kim |
| 6,370,841 B1 | 4/2002 | Chudy et al. |
| 6,377,867 B1 | 4/2002 | Bradley et al. |
| 6,383,123 B1 | 5/2002 | Ehring et al. |
| 6,446,416 B1 | 9/2002 | Kuhn et al. |
| 6,449,927 B2 | 9/2002 | Hebron et al. |
| 6,474,635 B2 | 11/2002 | Ruf et al. |
| 6,522,945 B2 | 2/2003 | Sleep et al. |
| 6,564,121 B1 | 5/2003 | Wallace et al. |
| 6,597,969 B2 | 7/2003 | Greenwald et al. |
| 6,625,952 B1 | 9/2003 | Chudy et al. |
| 6,687,676 B1 | 2/2004 | Denny |
| 6,711,460 B1 | 3/2004 | Reese |
| 6,728,684 B1 | 4/2004 | Reichert |
| 6,742,671 B2 | 6/2004 | Hebron et al. |
| 6,847,861 B2 | 1/2005 | Lunak et al. |
| 6,883,681 B1 | 4/2005 | Coughlin et al. |
| 6,892,512 B2 | 5/2005 | Rice et al. |
| 6,910,601 B2 | 6/2005 | Thomas |
| 6,964,146 B2 | 11/2005 | LaRocca |
| 6,970,769 B2 | 11/2005 | Rice et al. |
| 6,983,579 B2 | 1/2006 | Rica et al. |
| 7,006,893 B2 | 2/2006 | Hart et al. |
| 7,010,388 B2 | 3/2006 | Lunak et al. |
| 7,010,899 B2 | 3/2006 | McErlean et al. |
| 7,058,584 B2 | 6/2006 | Kosinski et al. |
| 7,072,737 B2 | 7/2006 | Lunak et al. |
| 7,100,792 B2 | 9/2006 | Hunter et al. |
| 7,110,855 B2 | 9/2006 | Leishman |
| 7,121,427 B2 | 10/2006 | Guerra |
| 7,123,989 B2 | 10/2006 | Pinney et al. |
| 7,185,477 B2 | 3/2007 | Rice et al. |
| 7,249,688 B2 | 7/2007 | Hunter |
| 2003/0200726 A1 | 10/2003 | Rast |
| 2004/0040975 A1 | 3/2004 | Hunter et al. |
| 2004/0064215 A1 | 4/2004 | Greeven et al. |
| 2004/0088187 A1 * | 5/2004 | Chudy .................. G16H 20/10 705/2 |
| 2005/0021173 A1 | 1/2005 | Pinney et al. |
| 2006/0086640 A1 | 4/2006 | Luciano et al. |
| 2007/0162179 A1 | 7/2007 | Freudelsperger |
| 2007/0270998 A1 | 11/2007 | Luciano, Jr. et al. |
| 2008/0006647 A1 | 1/2008 | Hunter et al. |
| 2008/0136187 A1 | 6/2008 | Christ |
| 2008/0190953 A1 * | 8/2008 | Mallett .................. B07C 7/005 221/13 |
| 2008/0312957 A1 | 12/2008 | Luciano et al. |

OTHER PUBLICATIONS

Chinese Office Action dated Aug. 20, 2013, in China Patent Application No. 200980155637.5 (with Partial English translation).
Mexican Office Action dated Sep. 2, 2014 in Patent Application No. 2011/005873 with English Translation.
Australian Office Action dated Mar. 17, 2015 in Parent Application No. 2009322199.
Korean Office Action dated Mar. 17, 2016 in Patent Application No. 10-2011-7018449.
Extended European Search Report dated May 6, 2016 in Patent Application No. 09831183.0.
Office Action dated Jul. 5, 2016 in Canadian Patent Application No. 2,745,147.
Office Action dated May 23, 2017, in Canada Patent Application No. 2,745,147.
Office Action dated Nov. 20, 2017 in Canada Patent Application No. 2,745,147. (3 pages).
Search Report dated Jul. 26, 2018, in European Patent Application No. 09 831 183.0-1217 (7 pgs.).
Office Action dated May 13, 2019, in Canada Patent Application No. 2,989,635 (4 pgs.).

(56) References Cited

OTHER PUBLICATIONS

Office Action dated Jul. 5, 2019 in Brazilian Application No. PI0920964-6 with English Translation.
International Searching Authority, The International Search Report and The Written Opinion of the International Searching Authority, or the Declaration, PCT/US2009/066756, dated Feb. 1, 2010, 22 pages.

* cited by examiner

SYSTEM AND METHODOLOGY FOR FILLING PRESCRIPTIONS

This Application is a Continuation of U.S. application Ser. No. 12/617,075, filed Nov. 12, 2009, allowed, which claims priority to U.S. Provisional Patent Application Ser. No. 61/120, 209, filed Dec. 5, 2008 and hereby incorporated by reference in its entirety. This is also a continuation in part of U.S. patent application Ser. No. 12/559,630 and Ser. No. 12/559,601, each filed Sep. 15, 2009 and hereby also incorporated by reference in its entirety.

BACKGROUND i. Field

This invention is directed to a process or method for processing prescriptions and dispensing medications and nutritional supplements to be taken orally in long-term care and other institutional settings.

ii. Related Art

Individuals are taking an ever increasing variety and number of both supplements and medications. Each of these individuals has very unique requirements as to the type and concentration of medications being taken. However, pharmaceutical manufacturing and distribution systems are designed for mass distribution in large quantities and have not addressed these individualized needs.

Automated dispensing of prescription medications, such as oral solid pills and liquid unit-of use ampules, is a well-known method of filling dosage-based prescriptions. Dosage-based prescriptions are filled in a way which organizes the medication into one or more dosage units by, for example, the time of day at which the medication is to be taken (med pass) or the sequence in which the medication is to be taken. Dosage-based automated medication dispensing systems have particular utility in settings where large amounts of such prescription medications are required. Hospital and other institutional formularies are ideal candidates for use of such dispensing systems. However, other businesses, such as mail order prescription filling services and pharmacies, can also use these systems.

Automated medication dispensing systems typically include one or more computer-controlled dispensing machines which store and dispense medications according to patient-specific prescription information. These automated medication dispensing devices offer many advantages. These advantages include the ability to store a broad range of prescription medications and the ability to fill patient prescriptions in a high volume manner. In addition, use of automated prescription filling equipment may reduce the possibility of human error in filling patient prescriptions. Another advantage is that the cost savings from automated dispensing of medications can be used to employ more pharmacists and care givers who can provide personalized service to the patients.

However, known automated medication dispensing systems have significant disadvantages. For example, certain dosage based systems are unable to fully utilize bulk medication dispensing technology. Bulk dispensing of medications involves the storage of pills or medications in bulk, for example in bins, magazines or canisters. The bulk-dispensed medications may be dispensed into containers according to patient-specific prescription information. As can be appreciated, bulk dispensing is most efficient when the medication is stored in a raw, non-prepackaged form since this permits great flexibility in the type of medications which can be dispensed and because the medications can be rapidly replenished in the bulk storage containers. Bulk dispensing becomes problematic when the medications are poorly and ineffectively processed in the dispenser. Commonly, the pills are mishandled, become jammed or clogged in the machine and/or are difficult to track and inventory.

Many prior art systems which provide bulk storage of individual supplements or medications do not efficiently, effectively and reliably dispense those medications and supplements to fill a patient's order. This is disadvantageous because it is difficult to arrange, customize and/or mix the bulk supplies of pills for the patient's requirements. The process also requires time-consuming and expensive inventory control of the medications to be dispensed to avoid expiration and tracking issues. Such bulk-based systems are unable to realize the flexibility and cost savings benefits of automated dispensing.

Another disadvantage of certain prior art bulk medication dispensing systems is that it is difficult to fully control and track the individual dosage units. The bulk medications used by these systems do not have information which is generated for the specific medications or supplements for each patient as the medication is dispensed. Such information might include National Drug Code ("NDC") information and a code for the storage location of the medication within the dispensing system. This information is limited and leaves little room for application of more patient-specific information such as the patient's name and other information which directly links the patient to the medication.

There are many potentially useful applications for the patient-specific information. For example, this information can be used at the completion of the filling process to verify that the correct medication has been supplied to the patient. The information could be used at the patient's bedside to create a record of the medication taken by the patient including the type and quantity of medication taken and the time of day or med pass at which the medication was taken.

It would be a significant improvement in the art to provide an automated method for processing prescriptions and dispensing medications in dosage form with real-time-generated machine-readable code so that the medication could be associated with a specific patient.

Additional problems exist with the current manner of dispensing these medications and supplements. The user or institution needs to keep track of times at which doses are to be taken, and remember to take or administer each of the doses. Often, a patient will forget either to take a dose, or forget that they have taken a dose, wherein they take an additional dose or miss a dose. Misdosing is very prevalent amongst senior citizens, especially the millions suffering from memory loss, or Alzheimer's disease.

Requiring individuals to collect and dispense from their own medicine cabinets is subject to a significant degree of risk. Medications are forgotten, taken incorrectly, mixed improperly, and so forth. It is onerous to many senior citizens who must deal with the most complex assortment of medications and supplements. Due to the difficulties with orchestrating each pill dose, it is not surprising how often people forget, or make dosing mistakes with even their most important medications.

Institutional care organizations, such as hospitals, long-term care facilities, nursing homes, and the like, suffer from additional problems associated with providing doses of supplements and medications to their patients. Institutions have a staff which maintains the various supplements and medications distribution to the patients. The overhead and liability associated with creating and supervising the prescriptions and these numerous doses each day for every patient becomes exceedingly costly and prone to error. It will certainly be appreciated that the inventory of supplements and medications at an institution must be carefully managed to assure adequate supplies, proper storage conditions, proper dispensing conditions, prevent theft, and assure that expiration dates are taken into account. Care providers and staff need to remain vigilant to be certain that each patient gets the proper doses, and that doses created for one patient are not received by another patient. Misdosing of patients within an institutional setting can have dire consequences.

Another problem arises when a patient's prescription changes and dosing has already been prepared for the patient. Pre-packaged multiple medications are one option that is difficult to implement because the pre-packaging of multiple medications for use over a period of time is a specially service that has not been successfully automated to date. The manual processing of prescription orders is expensive because the process lacks automation. Therefore, there is a need for an automated ordering system and process that is simple and cost effective for a patient or a pharmacist to use. An automated system and method for receiving orders would make it substantially easier to process a multiple prescription order, which would in turn make the process much more cost effective. In the event the patient is discharged or the treatment is changed, the unused portion of a prepared multi-day supply cannot be cost effectively reused even though the product may be labeled appropriately. The labor cost required for reintroducing the medications and supplements into the system and maintain the integrity and traceability of manufacturer and expiration data exceeds the value of the medicine/supplement, even if the substantial restocking fees are paid by the healthcare system. As a result, such unused medications and supplements are returned to the pharmacy for disposal. This disposal of unused medications and supplements is a significant waste of those resources as well as a detriment to the environment.

As can be seen, therefore, the development of an improved method for processing and dispensing both consumers and institutions that would eliminate the necessity of wasting unused medications while increasing safety and convenience is needed. Moreover, a convenient and efficient way for patients, pharmacists, and physicians to order multi-drug prescriptions from a pharmaceutical dispensing system which produces multi-dose prescriptions is needed.

SUMMARY

This invention solves these and other problems in the prior art by providing in one embodiment an overall pharmacy system and methodology in which bulk medications and supplements are introduced into the work flow, individually packaged and assembled into med pass orders per patient and delivered to the long-term care (LTC) facility or other institution for patient consumption.

The process according to one embodiment of this invention begins by converting bulk medications and supplements to packaged unit doses and ultimately individually packaged med pass bags for each patient on a 24-hour schedule. Additionally, inventory management is automated and the various safeguards and measures built into this system increase patient safety eliminate waste and increase labor efficiency by reducing and/or minimizing the disposal of unused medications and supplements.

One objective of this system and methodology is to avoid the need for disposal of prescriptions medications and nutritional supplements thereby attacking the waste and inefficiency issues at their source. The strategy and approach utilized by this invention is much more comprehensive than just a medication and nutritional supplement automated dispenser. The comprehensive strategy employed by this invention to the efficient and economical distribution of medications and supplements begins with logging into an inventory database the bulk medications and supplements before each of the individual doses are packaged and then assembled in a unit dose storage tube in conjunction with pharmacist review. A fill event server is updated at each step in the process and positive control of each unit dose package is maintained throughout the entire process. In other words, gravity feed and the random nature of bulk or loose pills and other medications freefalling through or clogging the system is avoided in the approach adopted by this invention.

After the unit dose storage tubes are prepared and entered into the inventory database, they are loaded into the dispenser for the automated filling and packaging of individual med pass patient orders. The dispenser provides an automated solution to the efficient and timely preparation of med pass orders handled in LTC and assisted living settings by filling individual med pass orders for each patient and assembling them in a bag of unit dose medications and supplements and combining individual bags together. The dispenser is typically located remotely from the LTC facility and will serve multiple facilities. The bags are then packed in a tote and delivered to the LTC for distribution. At each step in the process, the unit dose medications and supplements are tracked via a bar code scanner and the status of each unit dose medication is cataloged and regularly updated in the pharmacy information management system (PIMS) database.

The design of the overall system and its individual components allows for physical control of each unit dose package from start to finish without any unit dose package "free fall" in the system. This process is automated and does not rely upon manual sorting. The med pass bags are consolidated into the final shipping container and do not require manual sorting and packing thereby solving many of the problems associated with prior art solutions.

BRIEF DESCRIPTION OF THE DRAWINGS

The above-mentioned and other features and advantages of these inventions, and the manner of attaining them, will become more apparent and the invention itself will be better understood by reference to the following description of embodiments of the invention taken in conjunction with the accompanying drawings, wherein.

DETAILED DESCRIPTION

The detailed description exemplifies specific embodiments of the invention which are described in sufficient detail so as to allow a person of ordinary skill in the art to practice the invention without undue experimentation. It will be appreciated that the apparatus and associated method may vary as to configuration and as to details of the parts and steps without departing from the basic concepts as disclosed herein. While the invention is susceptible to various modifications and alternative forms, a specific embodiment thereof is shown by way of example in the FIGURES and will herein be described in detail. It should be understood, however, that there is no intent to limit the invention to the particular form disclosed, but on the contrary, the invention is to cover all modifications, equivalents, and alternatives falling within the spirit and scope of the invention as defined by the claims.

Figure 1:
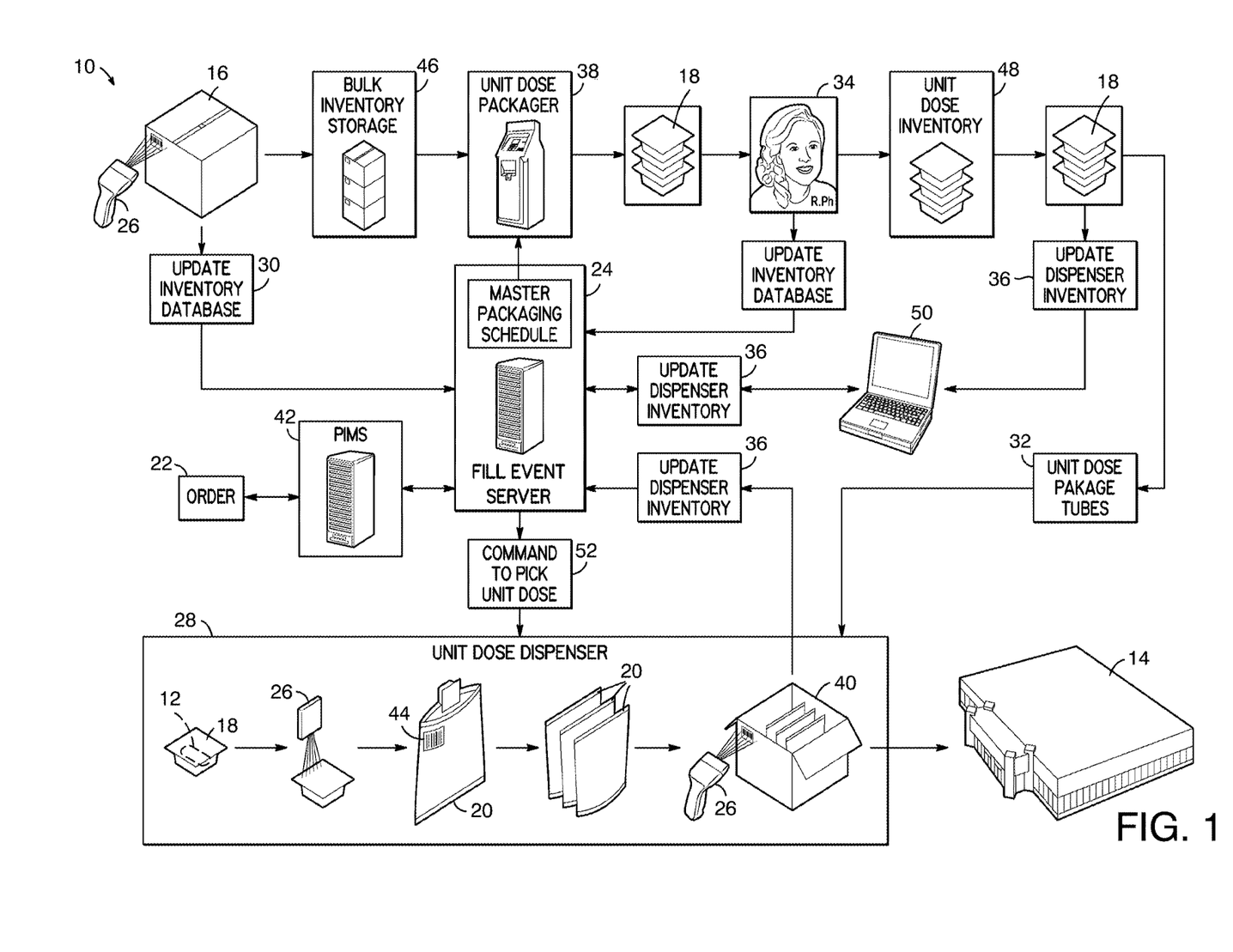
FIG. 1 is a schematic representation of one embodiment of a methodology and associated system components for automated fulfillment of patient prescriptions for a long term care facility according to this invention.

Referring to FIG. 1, this invention is generally directed to a process or method and associated system and sub-systems 10 to provide a turnkey solution for dispensing solid medications and nutritional supplements 12 to be taken orally in health care settings, including but not limited to long term care (LTC) and assisted living settings 14. The process begins by converting bulk medications and supplements 12 to individual packaged unit doses 18 and ultimately individually packaged med pass bags 20 containing the prescribed medications and supplements 12 for each patient on a 24-hour schedule. Generally, this invention is directed to a process 10 for filling prescriptions which begins with receiving an order 22 by the system 10. Additionally, inventory management is also automated via a master packaging fill event server 24. The various safeguards and measures built into the system of this invention include unit dose scanning at various steps as well as personal inspections, as needed, to increase patient safety, eliminate waste and increase labor efficiency by reducing and/or minimizing the disposal of unused medications and supplements.

The system and associated method 10 of this invention is used to dispense unit dose oral solid medications and supplements 12 within a LTC facility 14 based on a twenty-four (24) hour fill cycle. The system 10 is capable of handling vials as an added feature should the system require and so demand. The medications and supplements 12 are delivered by the pharmacy within the LTC to the LTC facility patients. The system 10 is designed to fulfill cycle-fill orders, new prescription orders, PRN orders, ER box restock orders and leave of absence orders in both manual and STAT delivery modes.

One objective of this system and methodology 10 is to avoid the need for disposal of unused medications and supplements 12 thereby attacking the waste and inefficiency issues at their source. The strategy and approach utilized by this invention utilizes a unit dose dispenser 28, but the invention is much more comprehensive than just the medication and nutritional supplement automated dispenser 28 that may be utilized. The comprehensive strategy employed by this solution to the efficient and economical distribution of medications and supplements 12 begins with logging into an inventory database 30 the bulk medications and supplements 12 before each of the medications and supplements 12 are initially placed in bulk inventory storage 46 or directly packaged in a unit dose packager 38 and then assembled in a unit dose tube 32 in conjunction with pharmacist review 34. A fill event server 24 is updated at each step in the process and positive control of each unit dose package 18 is maintained throughout the entire process 10. In other words, gravity feed and the random nature of medications freefalling through the system 10 is avoided in the approach according to this invention. After the unit dose storage tubes 32 are prepared and entered into the dispenser inventory database 36, they are loaded into the automated dispenser 28 for the assembling via automated filling and bagging of individual med pass patient bags 20.

The bulk medications and supplements 12 are individually packaged in unit dose packages 18 by a unit dose packager 38. The unit dose packager 38 in one embodiment of this invention includes a pill shuttle and magazine loader system (not shown) which seals individual medications/supplements 12 into blister packages, separates the blister packages into discrete lanes and loads the individual blister packages 18 into tubes 32. The unit dose packages 18 may be stored in inventory 48 prior to being placed in tubes 32 as demand indicates. Multiple tubes 32 may be filled simultaneously and once the tubes 32 are filled, they are verified by a pharmacist and upon proper verification, transferred to the unit dose dispenser 28 for dispensing to fill the individual prescription orders.

In one embodiment, the unit dose packager 38 utilized with this invention is manufactured by Pentapack N.A. Corp. (www.pentapackna.com) as Model BP515. The Pentapack packager packages medications and supplements 12 in the blister packages 18 and may be utilized in combination with a pill shuttle (not shown) to aid an operator in the loading of bulk medications and supplements 12 into the unit dose packager 38.

The tubes 32 filled with unit dose packages 18 are loaded into the dispenser 28. The dispenser 28 provides an automated solution to the efficient and timely preparation of med pass bags 20 handled in LTC and assisted living settings 14 by filling individual med pass orders for each patient and assembling them in a bag 20 of unit dose medications and supplements 12 and staking individual bags together as needed. The unit dose dispenser 28 may be located remotely from the LTC facility 14 and will serve multiple facilities 14. The staked bags 20 are then packed into a tote 40 and delivered to the LTC 14 for distribution. At each step in the process, the unit dose packages 18 are tracked via one or more bar code scanners 26 and the status of each unit dose package 18 is cataloged and regularly updated in the pharmacy information management system (PIMS) database 42.

The design of the overall system 10 and its individual components according to this invention allows for physical control of each unit dose 18 from start to finish without any unit dose "free fall" in the system. This process is automated via appropriate computer operations 50 and does not rely upon manual sorting. The med pass bags 20 are consolidated into the final shipping tote 40 and do not require manual sorting and packing. The fill event server 24 interfaces with the unit dose dispenser 28 to provide appropriate pick commands 52 according to the orders 22. It will be appreciated that although it is preferable to separately retain each of the unit doses within individual packages 18 which are assembled with one another in a given bag 20 such as date sequential for a single patient, med pass or by patient number (for multiple patients within an institutional setting); the medications and supplements 12 may be alternatively packaged in any convenient form which allows a set of medications or supplements 12 which was selected via the order 22 to be taken at a given time or med pass to be easily retrieved for use without departing from the invention.

Each individual bag 20 may be configured with an indicia 44 containing information about whom the individualized prescription has been created for, and the time that the dose is to be taken. For example each bag 20 may contain the name of who is to take the order, for example "Jane Doe" and their address, should the packet get misplaced, "1990 Paxit Drive, Columbus, Ohio 43230". Each Dose packet preferably contains the date and time the dose is to be taken, for example a series may appear as: "8:00 AM on Tuesday, Jun. 1, 2009", "2:00 PM on Tuesday, Jun. 1, 2009", "8:00 PM on Tuesday, Jun. 1, 2009", "8:00 AM on Wednesday, Jun. 2, 2009", . . . "8:00 PM on Tuesday, Jun. 29, 2009". The bag 20 may include additional information such as "Take with food" and any other precautions. Inserted instructions or content list may also be included within each bag 20. In addition, the bag 20 may contain information listing information about the medications or supplements 12 contained therein. The string of individualized bags 20 are placed in the tote 40 with any other portions of the order 22, and shipped to the LTC 14.

A user may submit an order 22 into the PIMS database 42 which order may originate from a consumer, patient, doctor, administrator or pharmacist via an internet enabled computer or appliance, accessing through the Internet, a web site hosted by a web server. Within the web site the individual can establish a dosing schedule by selecting the times during each day and the medications and/or supplements 12 to be taken at those times. The fill event server 24, which is associated with the system 10, receives the processed orders 22 from the PIMS 42. It will be appreciated that alternative forms of data communication, such as electronic data interchange, XML, and so forth may be utilized to allow the user to submit the order(s) to be processed by the system 10. Furthermore, the communication system may be integrated within, or operate in conjunction with an institutional computer system, such as a hospital, nursing-home, LTC and similar systems that may act as a user on behalf of a patient. It should also be appreciated that institutions often prefer their own interface wherein alternative communication protocols are established for communicating the dose information to the temporal dosing system without departing from this invention. Prescription orders 22 that are phoned in or sent in by facsimile can be entered into the PIMS 42 through a control terminal (not shown) by a local operator. Moreover, control terminal will also be used for performing maintenance on prescription processing system 10 and for interacting with and updating software programs on the system 10.

In one embodiment, the unit dose dispenser 28 which may be utilized with this invention is described in related patent application Ser. No. 12/559,630 and Ser. No. 12/559,601, each filed Sep. 15, 2009 and each incorporated by reference herein in its entirety.

A conveyor (not shown in FIG. 1) of the dispenser receives individual unit dose packages 18 from a series of dispensing modules and at a down-stream end of the conveyor, the unit dose packages 18 are deposited into a bag 20. The bag 20 is collected with other bags and the groups of bags are joined via heat and staked together. The staked bags 20 are then loaded into a tote 40 and once the tote 40 is filled, it is automatically labeled, verified through a scanner 26 and delivered to the LTC 14 for consumption by the patients. The inventory of the dispenser 28 is updated 36 as reflected in the fill event server 24.

Figure 2:
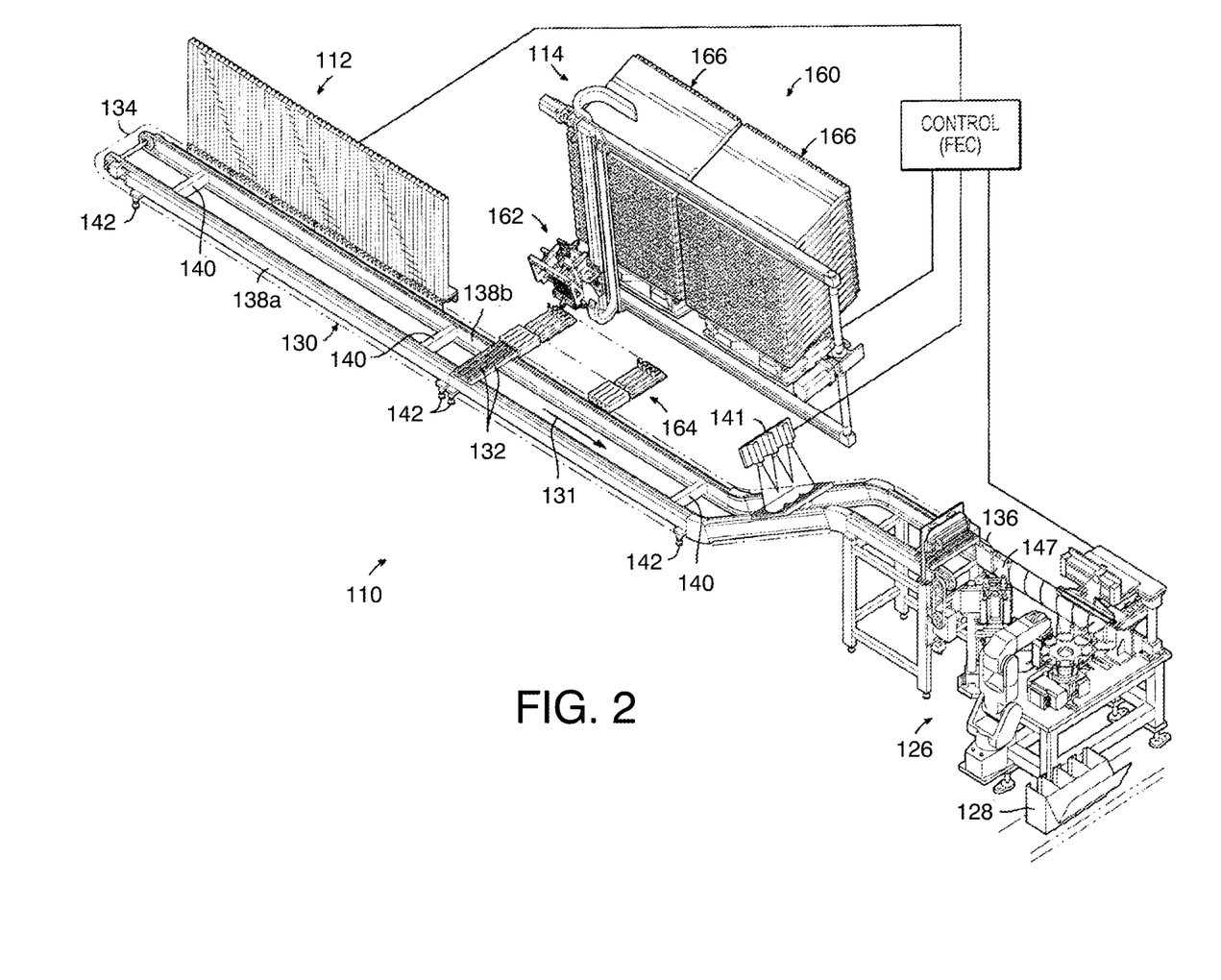
FIG. 2 is a perspective view of an exemplary system for storing and dispensing medications and supplements in accordance with the present disclosure.

FIG. 2 depicts an exemplary automated dispensing system 110 in accordance with the principles of the present disclosure. In the embodiment shown, the dispensing system 110 is configured to store and dispense individually packaged and labeled doses of medications/supplements, and to assemble the dispensed medications/supplements into individual medication orders, such as time-pass medication orders to be delivered to a long-term care facility, for example. It will be appreciated, however, that a dispensing system in accordance with the present disclosure may alternatively be configured to dispense other items. The dispensing system 110 is divided into distinct modules that are dedicated to dispensing the medications/supplements based on the demand, or order frequency, of those items. In the embodiment shown, a first module 112 is configured to dispense medications/supplements having a relatively high demand or order frequency, and a second module 114 of the dispensing system 110 is configured to store and dispense medications/supplements having a relatively lower demand or order frequency.

With continued reference to FIG. 2, the dispensing system 110 further includes an endless conveyor 130 comprising a plurality of carriers 132 that move past the first, high-demand module 112 and the second, low-demand module 114 to collect ordered medications/supplements and carry them to a designated location for further processing. In the embodiment shown, a first end 134 of the conveyor 130 is positioned adjacent the high-demand module 112. The carriers 32 are moved along the conveyor 130 past the high-demand module 112 and the low-demand module 114 toward a second end 136 where the medications/supplements are packaged for delivery to a long term care facility. In the embodiment shown in FIG. 2, the conveyor 130 comprises a pair of oppositely disposed, longitudinally extending rails 138*a*, 138*b* supporting the plurality of carriers 132. The conveyor 130 may further comprise cross-members 140 extending between the rails 138*a*, 138*b* and support legs 142 configured to support the longitudinally extending rails 138*a*, 138*b* a distance above a floor surface.

Figures 3, 4:
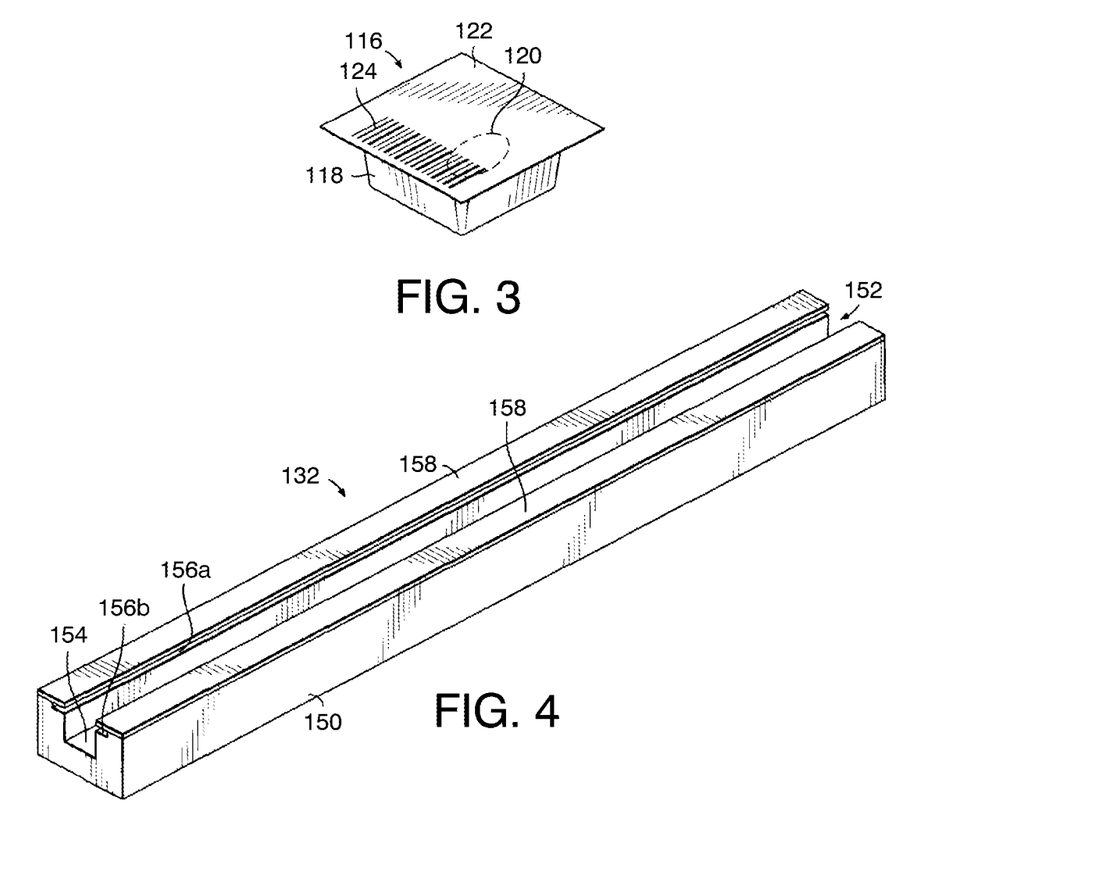
FIG. 3 is a perspective view of an exemplary package for containing a single dose of a medication/supplement in accordance with the present disclosure.
FIG. 4 is a perspective view of an exemplary carrier of a conveyor in accordance with the present disclosure.

In one embodiment, the medications/supplements are provided in packages 116 sized to receive an individual dose of a particular medication/supplement, commonly referred to as a blister pack. With reference to FIG. 3, an exemplary package 116 comprises a base portion 118 defining a cavity for receiving the individual dose of the medication/supplement 120, and a generally planar closure 122 disposed over an open end of the base portion 118. The packages 116 may be provided with information 124 related to the medication/supplement 120 contained in the packages 116, such as the name of the medication/supplement 120, the manufacturer, the date manufactured, the lot number, and/or other information. In the embodiment shown, information 124 is provided on the closure 122 and includes machine-readable information, such as a bar-code, that may be used to facilitate the automated storing, tracking, dispensing, and packaging of orders.

Figure 5:
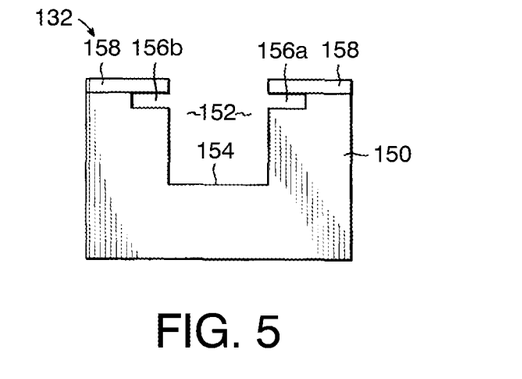
FIG. 5 is an end elevation view of the carrier of FIG. 4.

FIGS. 4 and 5 depict an exemplary carrier 132 comprising an elongate, generally rectangular body 150 having a longitudinal channel 152 formed into one side and extending between the ends of the body 150. The channel 152 is shaped complementarily to the shape of the packages 116 and includes a deep central portion 154 and shallower side portions 156*a*, 156*b* disposed on opposite sides of the central portion 154, whereby a package 116 can be received in the channel 152 with the base 118 positioned in the central portion 154 and the sides of the closure 122 supported on the side portions 156a, 156b. The side portions 156a, 156b are enclosed at their upper ends, such as by top plates 158 or other structure so that packages 116 received in the channel 152 are constrained for movement only along a longitudinal direction of the channel 152.

Figure 6:
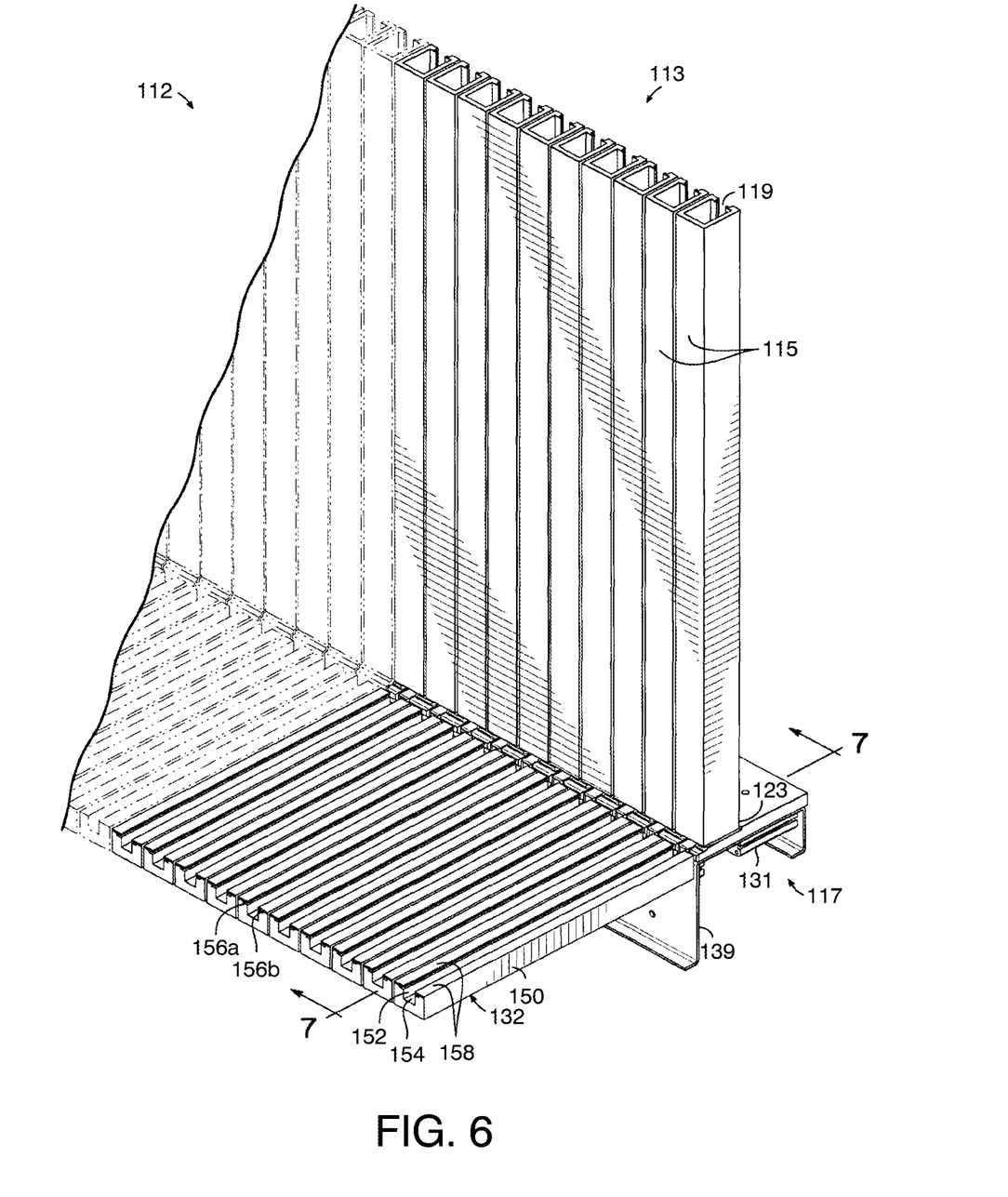
FIG. 6 is a perspective view of a first dispensing module and an adjacent portion of a conveyor of the dispensing system of FIG. 2.

As shown in FIGS. 2 and 6, the first or high-demand module 112 of the dispensing system 110 is located upstream from the second or low-demand module 114 along the conveyor path 131 of the conveyor 130 and travel of the carriers 132. The high-demand module 112 in one embodiment includes two units or banks 113 of storage tubes 115, each positioned on opposite sides of the conveyor 130, although only one unit 113 is shown in FIGS. 2 and 5 for clarity. Each unit 113 of the high-demand module 112 includes a number of vertically oriented storage tubes 115 such that the unit dose packages 116 in each tube 115 are stacked vertically one upon another. The unit dose packages 116 are loaded in storage tubes 115 in a generally vertical stack and similarly oriented with the base portion 118 depending downwardly from the upper planar closure portion 122 of the package 116.

The low-demand module 114 is downstream from the high-demand module 112 (FIG. 2) and may include two banks or units 166 of medication/supplement storage tubes 174, one unit 166 positioned on each lateral side of the conveyor 130 although the units 166 on only one side of the conveyor 130 are shown in FIG. 2 for clarity. As is the case with the high-demand module 112, the units 166 may feed unit dose packages 116 to the opposite ends of the carriers 132, although this is not accomplished simultaneously from the opposite ends of the carriers to inhibit the unit dose packages 116 from being pushed to the opposing unit 166.

Figure 7:
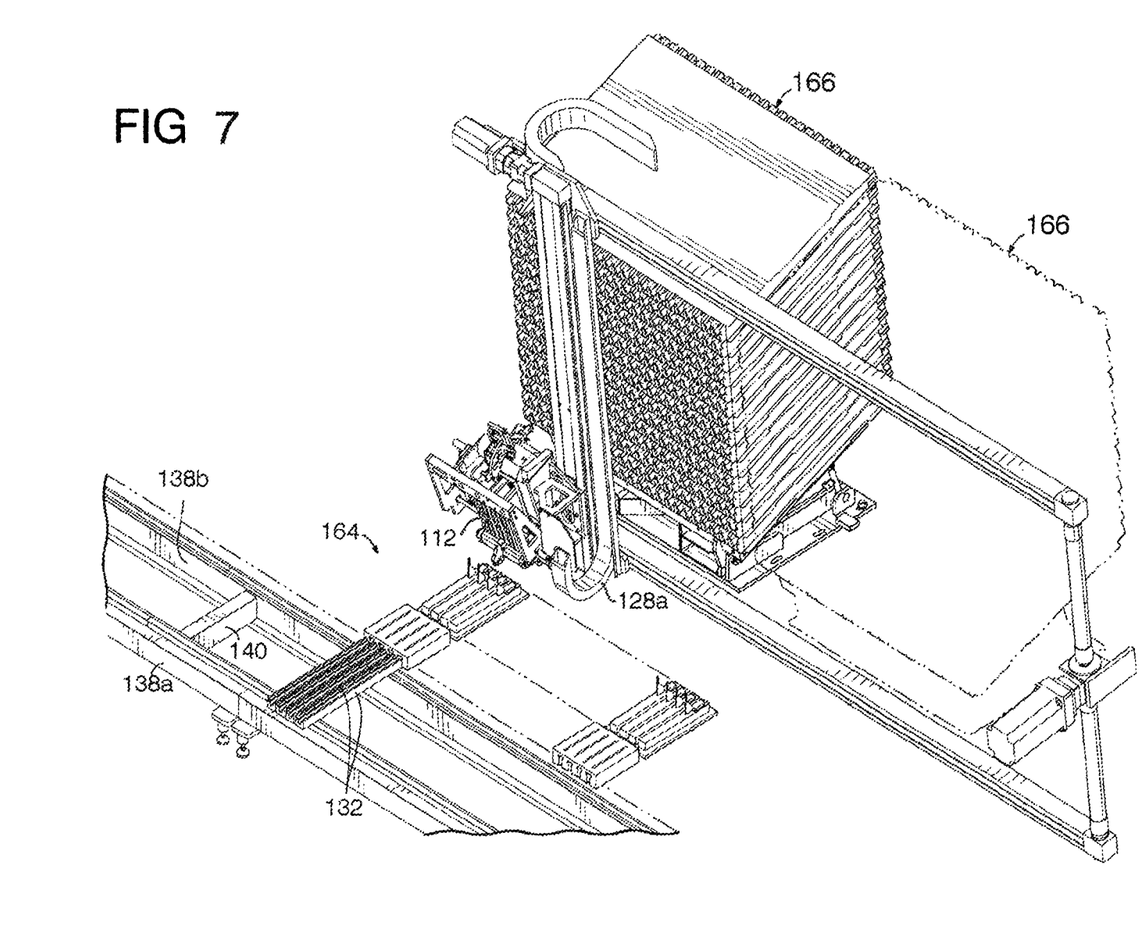
FIG. 7 is a perspective view of one embodiment of a second dispensing module of the dispensing system of FIG. 2 according to one embodiment of the present disclosure.

Referring now to FIG. 7, the low-demand module 114 includes a storage module 160 for storing the individually packaged and labeled medications/supplements, a pick device 162 for retrieving selected medications/supplements from the storage module 160, and a transfer station 164 for delivering the selected medications/supplements to the carriers 132 of the conveyor 130 to fill orders. The storage module 160 has one or more storage units 166 positioned alongside the conveyor 130, as may be desired, to accommodate storage of the medications/supplements needed to fill the medical orders.

When the carriers 132 on the conveyor 130 that are assigned to a particular order are aligned with slots on a transfer station 164 adjacent the conveyor 130 in the low-demand module 114 that contain the packages 116 for that particular order, the medications/supplements 120 are pushed into the assigned carrier 132. The assigned carrier 132 may already have unit dose packages 116 therein from the upstream high-demand module 112.

The conveyor 130 thereafter carries the carriers 132 to the packaging station 126 for final packaging and assembly of the patient orders. During movement of the packages 116, the carriers 132, transfer nests, and transfer stations are each configured to maintain positive control of the medications/supplements 120 such that no medication/supplement 120 is allowed to "free fall" during the dispensing process.

From the above disclosure of the general principles of the present invention and the preceding detailed description of at least one preferred embodiment, those skilled in the art will readily comprehend the various modifications to which this invention is susceptible.

Therefore, we desire to be limited only by the scope of the following claims and equivalents thereof.

The invention claimed is:

1. A system for processing prescription orders for patients of multiple medications, each medication stored in an individual container, comprising:
an inventory dispensing apparatus that
receives a patient's prescription order for a plurality of identified medications,
selects a number of the individual containers required to fulfill the prescription order, and
dispenses, through a discharge assembly, and while maintaining physical engagement of the individual containers throughout the dispensing and based on the selection, the number of the individual containers including the plurality of identified medications to a packaging apparatus; and
the packaging apparatus that
performs a packaging process by assembling the dispensed individual containers into a package, and
outputs the package corresponding to the patient's order,
wherein each individual container is a blister package having a base portion defining a cavity for receiving the individual dose of the medication and a generally planar closure, and
wherein the discharge assembly comprises channels which constrain movement of the individual containers.

2. The system of claim 1, wherein the channels constrain movement of the individual containers to allow movement only along a longitudinal direction of the channels.

3. The system of claim 1, wherein the channels have a cross-section corresponding to a cross-section of the individual containers.

4. A method for processing prescription orders for patients of multiple medications, each medication stored in an individual container, the method comprising:
receiving a patient's prescription order for a plurality of identified medications;
selecting from an inventory dispensing apparatus a number of the individual containers required to fulfill the prescription order;
dispensing from the dispensing apparatus to a conveyor, and while maintaining physical engagement of the individual containers throughout the dispensing, the number of the individual containers required to fulfill the prescription order;
conveying to a packaging apparatus, while maintaining positive physical control throughout the conveying, the number of the individual containers required to fulfill the prescription order;
assembling, using the packaging apparatus, the dispensed individual containers into a package; and
outputting, from the packaging apparatus, the package corresponding to the patient's order,
wherein the inventory dispensing apparatus comprises channels which constrain movement of the individual containers.

5. The method of claim 4, wherein each individual container is a blister package having a base portion defining a cavity for receiving the individual dose of the medication and a generally planar closure.

6. The method of claim 4, further comprising:
assembling identical medications after the pre-packaging and prior to the dispensing.

7. The method of claim 4, further comprising:
labeling each of the individual containers with relevant medication information.

8. The method of claim 4, wherein the channels constrain movement of the individual containers to allow movement only along a longitudinal direction of the channels.

9. The method of claim 4, wherein the assembling further comprises:
   bagging, using the packaging apparatus, the dispensed individual containers associated with a single order for each patient into a bag.

10. The method of claim 4, further comprising:
    accumulating, using the packaging apparatus, a plurality of the bags for a given patient, each bag being associated with a different order.

* * * * *